United States Patent [19]

Behling et al.

[11] Patent Number: 5,075,478

[45] Date of Patent: Dec. 24, 1991

[54] PROCESS FOR PREPARING PROSTAGLANDINS

[75] Inventors: James R. Behling, Lindenhurst; John R. Medich, Niles, both of Ill.

[73] Assignee: G. D. Searle & Co., Chicago, Ill.

[21] Appl. No.: 642,718

[22] Filed: Jan. 17, 1991

[51] Int. Cl.$^5$ .............................................. C07C 177/00
[52] U.S. Cl. ...................................... 556/441; 560/53; 560/121; 562/463; 562/503; 568/379
[58] Field of Search .................. 556/441; 560/53, 121; 562/463, 503; 508/379

[56] References Cited

PUBLICATIONS

Kitano, Chemistry Letters, 1987, 1523.

Behling, J., A.C.S. 110, 2642 (1988).

*Primary Examiner*—Robert Gerstl
*Attorney, Agent, or Firm*—Roger A. Williams; Paul D. Matukaitis

[57] ABSTRACT

A process for preparing prostaglandin derivatives by reacting a trans bis-tin ethylene with an organo metal compound then with a compound selected from an epoxide, aldehyde, or ketone, then, without isolation and in the same reaction vessel, reacting with an organo lithium compound, a cuprate complex and a cyclopentenone to produce a prostaglandin intermediate having an unprotected hydroxyl group on the omega side chain.

14 Claims, No Drawings

PROCESS FOR PREPARING PROSTAGLANDINS

BACKGROUND OF THE INVENTION

The invention herein is directed to a process for preparing prostaglandins of the PGE series. The invention herein is also directed to novel prostaglandin compounds and more specifically, prostaglandin intermediates or precursors.

Prostaglandin derivatives can be prepared utilizing vinylstannane compounds which are reacted with an alkyl lithium compound and subsequently with an organo copper compound and then with a cyclopentenone to provide the prostaglandin derivative. In such reaction the hydroxyl group on the omega side chain is protected. The vinylstannanes are employed to add the omega side chain of the prostaglandin derivatives, therefore it is important that the olefin geometry of the vinylstannenes be a trans configuration as the olefin geometry of the PGE prostaglandin derivatives is a trans configuration between the 13 and 14 carbon atoms.

U.S. Pat. Nos. 4,499,296; 4,322,543; 4,578,505; and 4,271,314 describe organo tin intermediates which are useful in the preparation of prostaglandin derivatives. U.S. Pat. Nos 4,777,275 and 4,785,124 describe higher order cuprate complexes which can be formed from vinylstannane compounds and which are then subsequently used in the production of prostaglandin derivatives.

A common method for synthesizing vinylstannanes involves the hydrostannylation of alkynes. This approach when used to produce prostaglandins has heretofore required the isolation, purification and protection of the intermediates. The term protection is used to signify the addition of a group to protect the hydroxyl groups which eventually result on the pentane ring and the omega side chain of the prostaglandin to be formed.

It would be desirable to provide a process for producing prostaglandins with sufficient specificity for the trans configuration in a one pot reaction wherein the steps of isolating, purifying and protecting the intermediates can be avoided.

SUMMARY OF THE INVENTION

The invention herein is directed to a process for preparing prostaglandins of the PGE series. The invention herein also includes novel prostaglandin intermediate compounds wherein the hydroxyl group on the omega side chain is unprotected and the hydroxyl group on the cyclopentane ring is protected.

The invention herein is directed to a process for preparing prostaglandin derivatives of the PGE series in a single reaction vessel. The process is performed by reacting a bis-tin ethylene of the formula $$R_3Sn\diagdown\diagup R_3Sn$$

wherein R is independently lower alkyl, alkenyl, phenyl, naphthyl, phenanthryl or thienyl; with an organo metal compound. The organo metal compound has the formula $$R^1M_n$$

wherein M is a metal selected from lithium, copper, and magnesium, n is either 1 or 2, and $R^1$ is selected from lower alkyl and an organo cuprate group having the formula wherein Y is —CN, —SCN, —OSO$_2$CF$_3$ or —S-phenyl, and $R_2$ is lower alkyl. The reaction of the bis-tin ethylene with the organo metal compound produces a metal vinylstannane intermediate. The metal vinylstannane intermediate is reacted, without isolation, with a compound selected from a ketone, aldehyde, alkyl halide and an epoxide to produce a metal alkoxide of the following formula for an epoxide $$R_3Sn\diagdown\diagup\diagdown\underset{R^6}{\overset{OM}{\underset{R^6}{|}}}R^6$$

for an aldehyde $$R_3Sn\diagdown\diagup\diagdown\underset{OM}{\overset{R^6}{|}}$$

and for a ketone $$R_3Sn\diagdown\diagup\diagdown\underset{R^6}{\overset{OM}{\underset{}{|}}}R^6$$

wherein M represent copper, lithium, and magnesium and $R^6$ is independently hydrogen, alkyl, alkenyl, phenyl, alkyloxy, phenoxy, and phenylaceto and substituted phenylaceto.

The metal alkoxide intermediate need not be separated but is reacted with a cyclopentenone of the formula wherein n is 0 or 1, wherein $R^3$ is an alkyl, alkenyl, or alkynyl group of 1 to 6 carbon atoms; $R^4$ is a protective group such as triethylsilyl, and $R^5$ is hydrogen or a lower alkyl group in the presence of an organo metal compound having the above formula $R^1M_n$ and wherein $R^1$ can also be 3,3 dimethyl 3 methoxy acetylene and a cuprate complex of the formula $$RCu(Y)Li$$

A PGE prostaglandin derivative is produced having an unprotected hydroxyl group on the omega side chain. Following exchange of hydrogen for the protective group $R^4$ a prostaglandin derivative is produced.

The invention herein is also directed to novel compounds which have particular utility as intermediates in the production of prostaglandin derivatives. The novel compounds herein have the formula

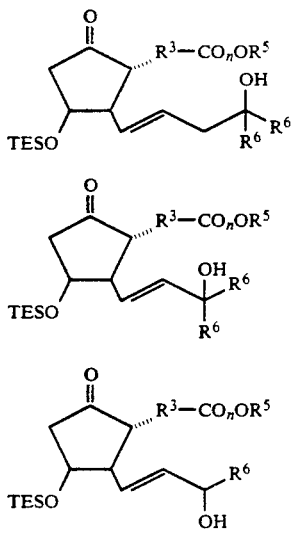

wherein $R^3$, $R^4$ and n have the above meanings and TES represents a triethylsilyl group.

DETAILED DESCRIPTION OF THE INVENTION

The invention herein is directed to a process for preparing PGE prostaglandin derivatives A benefit of using the process herein for the preparation of prostaglandin derivatives of the PGE series is that the prostaglandin derivatives can be prepared in a single reaction vessel utilizing a three component in situ cuprate reaction whereby two transformations are performed without isolating any intermediate. A particularly unique advantage of the process described herein is that the process produces essentially exclusively a trans stereo configuration for the PGE product as well as novel prostaglandin precursors which have an unprotected hydroxyl group on the omega side chain.

The process that is the subject of the invention herein can be illustrated with regard to the following reaction Scheme I:

vinylstannane metal complex (2). The organometal complex can be an organo lithium compound, organo copper, organo magnesium or an organo lithium complex such as a copper lithium or copper cyano lithium complex.

The vinylstannane metal complex is reacted with an epoxide, aldehyde or ketone ($E_1$) to produce a trans alkoxy vinylstannane (3) of the formula for an epoxide

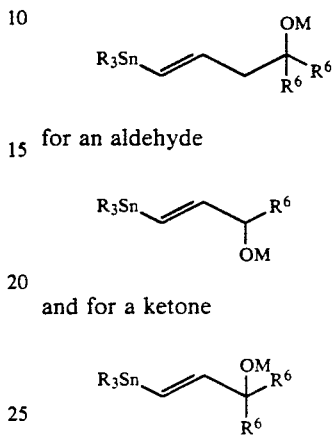

for an aldehyde and for a ketone wherein $R^6$ is independently hydrogen, alkyl, alkenyl, phenyl, alkyloxy, phenoxy, and phenylaceto and substituted phenylaceto. The alkoxy vinylstannane is a useful intermediate in the preparation of prostaglandin derivatives of the PGE series (5) as the compound is useful in producing the hydroxy substituted omega side chain of a prostaglandin derivative in a transformation reaction with an appropriate cyclopentenone.

As shown in reaction Scheme I, the trans alkoxy vinylstannane (3) is reacted, without isolation, with an organo lithium compound, a copper complex and an appropriately selected cyclopentenone, to produce the prostaglandin intermediate (4) of the formula when using an epoxide

SCHEME I

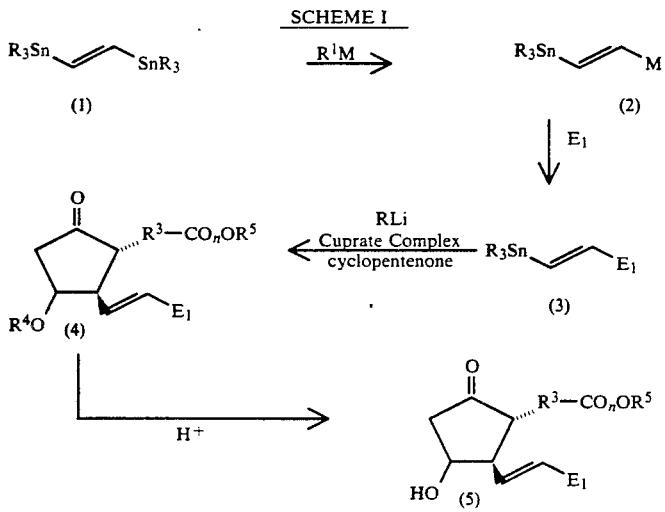

In the reaction Scheme I, a bis-tin ethylene (1) is reacted with an organometal complex to produce a

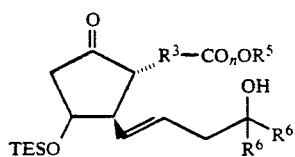

when using an aldehyde

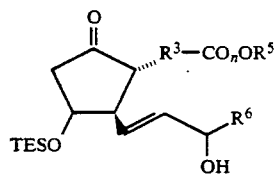

and when using a ketone

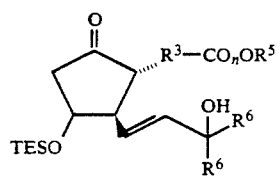

having a protected oxygen on the cyclopentenone moiety which can through a solvolysis reaction be converted to the desired prostaglandin derivative (5).

The reagent designated as $E_1$ in Scheme I can be an epoxide, an aldehyde or a ketone. Representative epoxides, aldehydes and ketones include the following

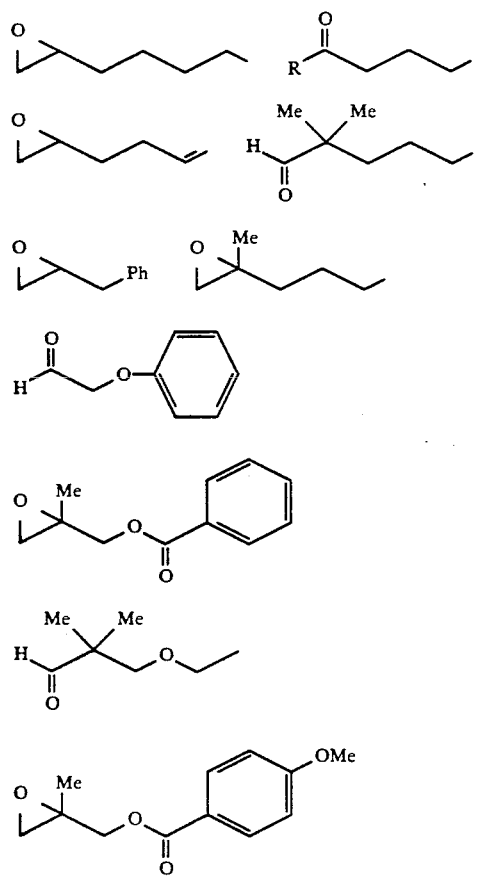

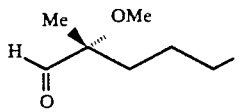

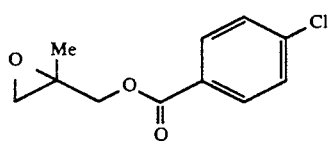

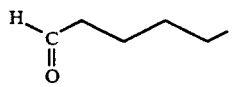

The cyclopentenone reactant has the following general structure

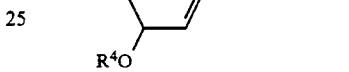

wherein n is 0 or 1 and $R^3$ is an alkyl, alkenyl, or alkynyl group of 1 to 6 carbon atoms and $R^5$ is hydrogen or a lower alkyl group. Representative upper side chains for a prostaglandin derivative can include the following:

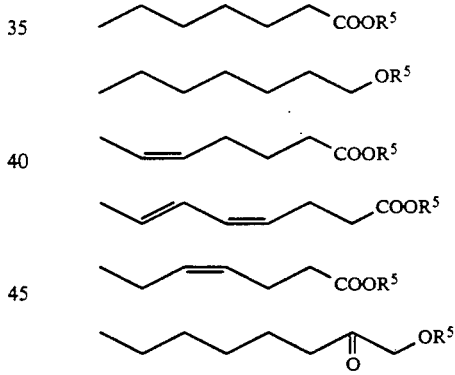

DESCRIPTION OF THE PREFERRED EMBODIMENT

The following reaction Scheme II shows a preferred embodiment of the process herein which can be preformed in a single reaction vessel without a need to isolate any intermediate. In the process a bis-rin ethylene (6) is reacted with a higher order cuprate organo lithium complex to produce a tin ethylene cuprate complex (7). The tin ethylene cuprate complex is reacted with a terminal epoxide to produce a trans β-alkoxy vinylstannane (8) which is not isolated. The trans β-alkoxy vinylstannane is reacted with an organo lithium compound, a higher order cuprate complex and a selected cyclopentenone (selected with the appropriate groups to provide the desired end PGE product) to produce the prostaglandin intermediate (9) which is subsequently transformed in the presence of acid to the PGE prostaglandin derivative (10).

SCHEME II

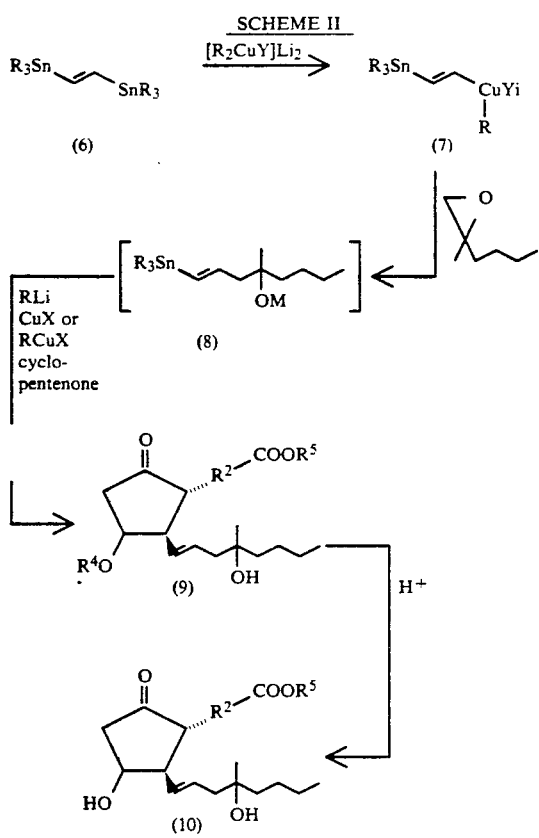

Referring to Scheme II, the bis-tin ethylene is a compound wherein R is independently lower alkyl, alkenyl, phenyl, naphthyl, phenanthryl, or thienyl. In a particularly preferred practice of the process herein, R is a lower alkyl and more particularly butyl, providing the compound (E)-bis (tributylstannyl)ethylene. The (E)-bis (tributylstannyl)ethylene is readily prepared according to the method of Mesmeyanov, A. N. and Borisof, A. E., *Dokl. Akad. Nauk. SSSR*, 1967, 174, 96. The compound can be prepared by the hydrostannylation of ethynyltributylstannane which is commercially available from Aldrich Chemical Company. The ethynyltributylstannane can itself be readily prepared according to the method of Bataro, J. C.; Hansen, R. N.; Seitz, D. E., *J. Org. Chem.*, 1967, 46, 5221.

The organo lithium complex which is preferably a higher order cuprate complex having the formula

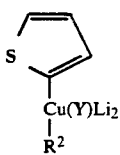

wherein Y is —CN,—SCN,—OSO$_2$CF$_3$ or —S-phenyl and R$^2$ is lower alkyl. Most preferably the higher order cuprate lithium complex is dilithiomethyl(2-thienyl)-cyanocuprate. The dilithiomethyl(2-thienyl)cyanocuprate is prepared by the addition of methyllithium to a solution of lithium 2-thienylcyanocuprate. Lithium 2-thienylcyanocuprate can be purchased from Aldrich Chemical Company or alternatively can be prepared in a solution of tetrohydrofuran (THF).

The use of the dilithiomethyl(2-thienyl)cyanocuprate produces a vinylstannane organo cuprate lithium intermediate which need not be isolated. This trans vinylstannane cuprate lithium complex is reacted with an epoxide, aldehyde or ketone to produce a trans β-alkoxy vinylstannane intermediate as shown in Scheme II which is not isolated. Any acceptable epoxide, aldehyde or ketone can be reacted with the vinylstannane cuprate lithium complex depending upon the end trans vinylstannane desired and thereby also the end PGE derivative desired. Those skilled in the art can readily discern and select the appropriate epoxide, aldehyde or ketone. Exemplary ketones, aldehyde and epoxides are shown above. The reaction of the vinylstannane cuprate lithium complex and the epoxide, aldehyde or ketone to create the regiospecific opening of the epoxide and the linking of the epoxide, aldehyde or ketone to the vinyl portion to displace the higher order cuprate lithium moiety from the vinylstannane is shown and discussed in Behling, J. R.; Ng, J. S.; Babiak, K. A.; Campbell, A. L.; Elsworth, E.; and Lipshutz, B. H., *Tetrahedron Letters*, 1989, 30, No. 1, pp 27–30. This resultant intermediate, a β-alkoxy vinylstannane, can be reacted without isolating it, with an organo lithium compound (such as described above), a lower order cuprate complex (such as MeCu(CN)Li) and a selected cyclopentenone to yield the protected intermediate (9) then subsequently acidified to produce the prostaglandin derivative (10). This subsequent reaction is detailed in U.S. Pat. Nos. 4,777,275 and 4,785,124. The trans vinylstannane compounds prepared can be reacted with cuprate complexes for addition to cyclopentenones as illustrated in *Journal of Medicinal Chemistry*, 29, 437 (1986) and *Journal of the American Chemical Society* (JACS) 1988, 110, 2641 of Behling et. al. to form prostaglandin derivatives as shown in Scheme II. The cyclopentenone is preferably a triethylsilyl protected cyclopentenone with the triethylsilyl group protecting the hydroxyl on the five member ring. That is, R$^4$ is preferably a triethylsilyl group.

The following examples are provided to illustrate the process for preparing prostaglandins and to illustrate the novel prostaglandin intermediates prepared by the process herein. These examples are given by way of illustration only and are not to be construed as limiting the invention, either in spirit or scope, as many modifications, both in materials and methods, will be apparent from this disclosure to those skilled in the art.

In the structures or formulas herein the solid triangular bond representation represents a bond extending outwardly from the plane of the paper on which it is drawn. In a similar manner, the series of dashes of decreasing length are used to represent a bond extending below the plane of the paper on which the structure is drawn. The curved bond representation represents that the hydroxyl group can be in either stereooptical position.

EXAMPLE 1

Preparation of lithium 2-thienylcyanocuprate.

To triply distilled thiophene (5.25 g, 62.5 mmol) in cold (−78° C.) anhydrous THF (24.7 ml, distilled from benzophenone ketyl) was added via syringe a solution of butyllithium (25.6 ml, 62.5 mmol, 2.4M in hexane) at such a rate that the internal temperature did not exceed −20° C. The resulting solution was stirred for 30 minutes, cooled to −60° C. and added to a cold (−60° C.) slurry of CuCN (5.59 q, 62.5 mmol, flame dried under argon) in anhydrous THF (64.7 ml). The resulting solution was allowed to warm to ambient temperature and then transferred to a dry Aldrich Sure Seal bottle and stored in a refrigerator at 5° C.

EXAMPLE 2

Preparation of

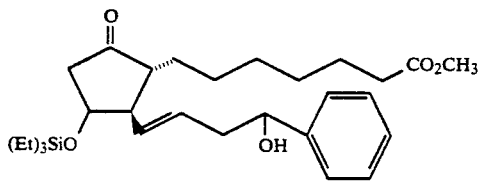

A 0.5M solution of 2 thienylcyanocuprate was prepared by adding 1.62 ml (3.90 mmol) of n-butyllithium (2.4M in hexane) to a solution of thiophene (0.33 g, 0.31 ml, 3.90 mmol) in 1.5 ml THF at −78° C. The solution was allowed to warm to −20° C. over 30 minutes, then cooled to −60° C. The resultant solution was added to a −60° C. slurry of 0.35 g (3.88 mmol) CuCN in 3.0 ml of THF. The resulting solution was allowed to warm to room temperature, then cooled to 5° C. Two milliliters of the solution was cooled to −10° C. and 0.78 ml (1.10 mmol) of methyllithium was added. After stirring for 5 minutes, (E)-bis(tributyl stannylethylene) (0.606 mg, 0.53 ml, 1.00 mmol) was added via syringe. The ice bath was removed and the mixture was allowed to warm to room temperature over a period of 30 minutes. The solution was cooled to −78° C. and 0.11 mg of styrene oxide (0.10 ml, 0.88 mmol) was added via syringe. After stirring for 10 minutes at −78° C., the reaction mixture was allowed to warm to 0° C. (approximately 45 minutes). The reaction mixture was cooled to −78° C. and 0.37 ml of n-butyllithium (0.88 mmol) was added. The reaction mixture was allowed to slowly warm to 0° C. (approximately 30 minutes). During this time and in a flame dried flask containing 82 mg of CuCN (0.92 mmol)in 3 ml THF at −10° C. was added 0.66 ml methyllithium (0.92 mmol) . The mixture was allowed to warm to 10° C., then cooled to a −5° C. and added to the vinyllithium solution which had been cooled to −78° C. After 5 minutes 0.16 ml of triethylsilyl protected cyclopentenone (0.44 mmol) was added. The solution was stirred for 10 minutes at −78° C. and the reaction was allowed to slowly warm to 0° C. (approximately 40 minutes). The reaction mixture was poured into 10 ml of a saturated ammonium chloride/ammonium hydroxide:9/1 and extracted with ethyl acetate. The ethyl acetate extract was stored over sodium sulfate overnight. The ethyl acetate extract was concentrated and the residue flash chromatographed with a mixture of ethyl acetate and hexane:10/90 yielding 150 mg of a yellow liquid. NMR analysis showed the residue to be the desired product.

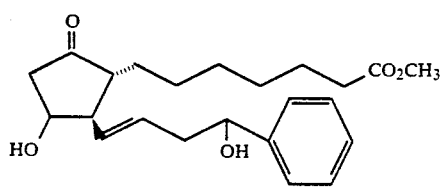

A quantity of 0.10g of triethylsilyl protected PGE as prepared in Example 2 is treated for 2 hours with 5.0 ml. of a 3:1:1 HOAC:THF: H2O solution. It is then extracted with two 5 ml. portions of heptane. The combined heptane extracts are washed with two 5 ml. portions of 3:1:1 HOAC:THF H2O and the combined aqueous phase is diluted with 15 ml. of water and extracted with three 15 ml portions of ETOAC. The ETOAC extracts are washed once with brine (5 ml.) dried over Na2SO4 and concentrated by rotary evaporation leaving the product as an oil. Chromatography with an appropriate solvent provides the product as an oil.

EXAMPLE 4

The procedures in Examples 2 and 3 are repeated in every essential detail with the exception that the triethylsilyl protected cyclopentenone has the following structure.

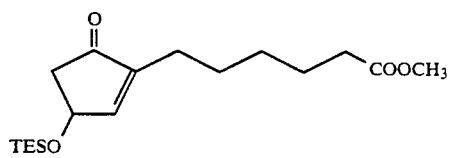

and the epoxide has the following structure

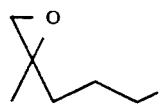

The resultant product has the following structure

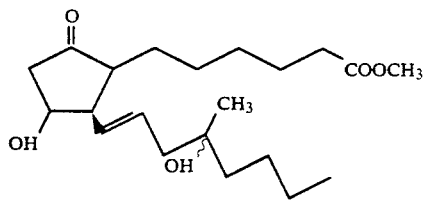

EXAMPLE 5

The procedures of Examples 2 and 3 are repeated in every essential detail with the exception that the triethylsilyl cyclopentenone has the following structure,

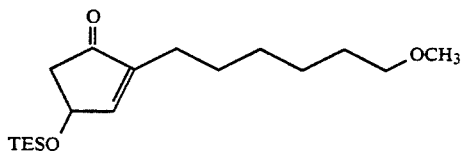

and the epoxide has the following structure

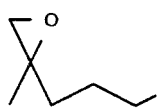

The resultant product has the following structure

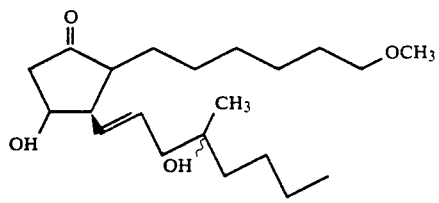

EXAMPLE 6

The procedures of Example 2 and 3 are repeated in every essential detail with the exception that the triethylsilyl cyclopentenone has the following structure,

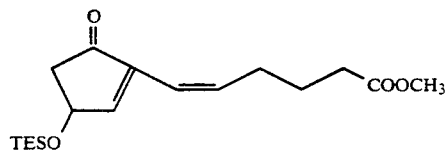

and the epoxide has the following structure

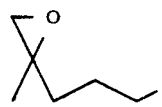

The resultant product has the following structure

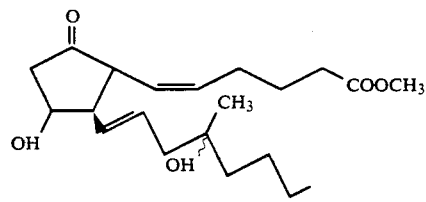

EXAMPLE 7

The procedures of Examples 2 and 3 are repeated in every essential detail with the exception that the triethylsilyl cyclopentenone has the following structure,

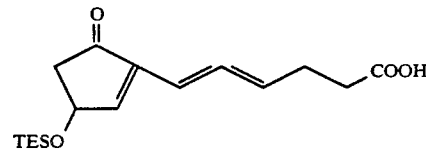

and the epoxide has the following structure

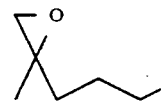

The resultant product has the following structure

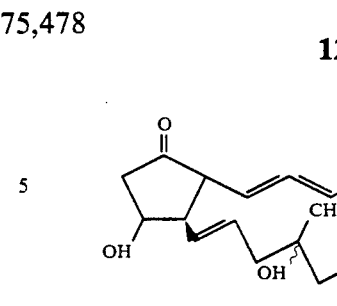

EXAMPLE 8

The procedure of Examples 2 and 3 are repeated in every essential detail with the exception that the triethylsilyl cyclopentenone has the following structure,

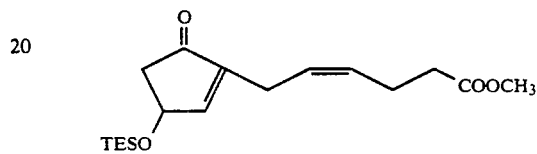

and the epoxide has the following structure

and the resultant product has the following structure

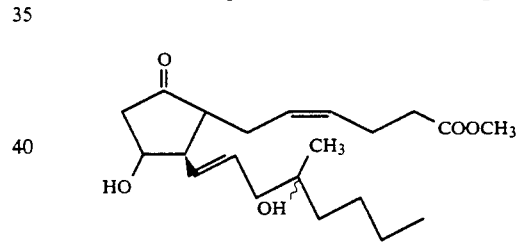

EXAMPLE 9

The procedures of Examples 2 and 3 are repeated in every essential detail with the exception that the triethylsilyl cyclopentenone has the following structure,

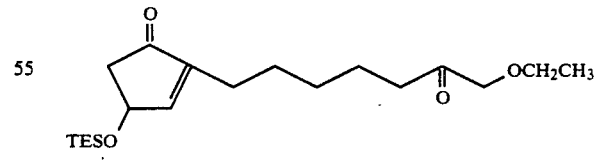

and the epoxide has the following structure

The resultant product has the following structure

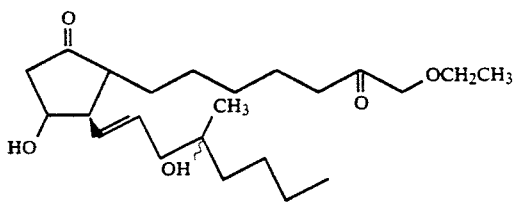

EXAMPLE 10

The procedures of Examples 2 and 3 are repeated in every essential detail with the exception that the triethylsilyl cyclopentenone has the following structure,

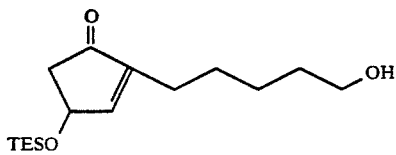

and the epoxide has the following structure

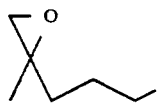

The resultant product has the following structure

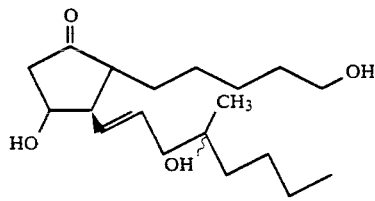

EXAMPLE 11

To a solution of bis-stannyl ethylene (1.2g, 1.06 ml, 2.00 m moles) in 4 ml of THF at −78° C. was added 0.8 ml (2.00 m moles) n-butyllithium (2.5M in hexane). The resulting solution was stirred for 1.5 hours at −78° C., then allowed to warm to −30° C. After cooling to −78° C., 4.0 ml of lithium 2 thienylcyanocuprate, 2-ThCu(CN)Li, solution (2.05M, 2.00 mmoles) was added. The mixture was stirred for 15 minutes then an epoxide having the following formula was added

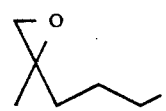

the reaction mixture was allowed to warm to 0° C. and was stirred at this temperature for one hour. The flask was tightly stoppered and placed in a refrigerator overnight. The reaction mixture was cooled to −78° C. and a solution of 2-lithiothiophene (2.00 mmoles) was added. The 2 lithiothiophene was prepared by the addition of n-butyllithium to thiophene in 2 ml THF at 78° C. and warming to −30° C. After stirring for 15 minutes 0.8 ml of n-butyllithium (2.5M in hexane, 2.00 mmoles) was added and the mixture was allowed to slowly warm to room temperature. After holding the mixture at room temperature for 10 minutes the mixture was cooled to −78° C. During this time a slurry of 0.18g CuCN (2.00 mmoles) in 2 ml THF was cooled to −28° C. and 1.4 ml of methyllithium (1.4M in ether,2.00 mmoles) was added. This solution was allowed to warm to room termperature and was added to the vinyl anion reaction mixture. After stirring for 5 minutes at 78° C., triethylsilyl protected norprostol

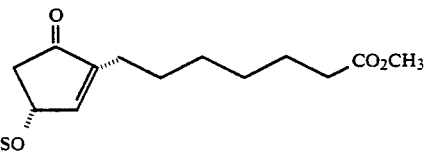

was added in an amount of 0.35 grams (1.00 mmoles) the mixture was stirred for 45 minutes at −78° C. The icebath was removed and the reaction was quenched by the addition of a 9/1 saturated NH4Cl/NH4OH solution. 25 ml of ethyl acetate was added and the mixture was stirred for 30 minutes. The layers were separated and the aqueous layer was extracted with two 25 ml portions of ethyl acetate. The combined organic extracts were washed once with 10 ml brine, dried over Na2SO4 and concentrated by rotary evaporation leaving a light brown liquid. The desired product was isolated by flash chromotography using 20/80 ethyl acetate and water to yield 0.16 grams of product.

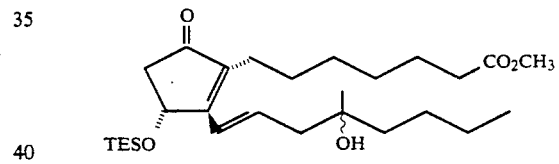

EXAMPLE 12

To a solution of bis-stannylethylene (1.2 grams, 1.06 ml, 2.00 mmoles) in 2 ml THF at −78° C. was added 0.80 ml of n-butyllithium (2.00 mmoles, 2.5M in hexane). The mixture was stirred for one hour at −78° C. then allowed to warm to −30° C. The reaction was held at this temperature for 15 minutes then cooled to −78° C. Hexanal (0.20g, 0.24 ml, 2.00 mmoles) was added and the mixture was stirred for 30 minutes at −78° C. TLC indicated that the hexanal was consumed during this time and 0.8 ml of n-butyllithium (2.5M in hexane, 2.00 mmoles) was added and the mixture was allowed to slowly warm to 0° C. During this time 1.5 ml of methyllithium (2.10 mmoles) was added to a slurry of CuCN in 2 ml THF at −5° C. and allowed to warm to 10° C. The resulting solution of MeCu(CN)Li was added to the hexanal reaction mixture which had been cooled to −78° C. The resulting mixture was not homogenous but contained some solid. The mixture was allowed to warm to −30° C. but the reaction still did not become homogenous. It was cooled to −78° C. and the protected cyclopentenone, TES-norprostol, was added in a amount of 0.35 ml (1.0 mmoles,) having the following formula:

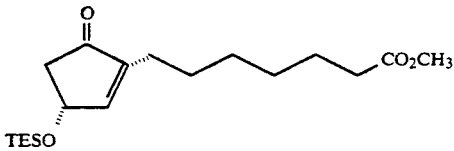

The resulting mixture was stirred for 30 minutes at −78° C. TLC showed that the product had formed. The reaction mixture was allowed to slowly warm to 0° C. (about 30 minutes) then was quenched by the addition of 10 ml of a 9/1 saturated solution NH$_4$Cl/NH$_4$OH solution. Ethyl acetate in a 25 ml aliquot was added and the mixture was stirred for 30 minutes. The layers were separated and the aqueous layer was extracted with two 15 ml portions of ethylacetate. The combined organic extracts were washed with brine (10 ml) and dried over Na$_2$SO$_4$ overnight. The solution was filtered and concentrated by rotary evaporation leaving 1.90 grams of a pale brown liquid. This material was flashed chromatographed using 15/85 ethylacetate/hexane as the eluent to yield 160 mg of product as a mixture of diasteriomers (35% yield) of the formula.

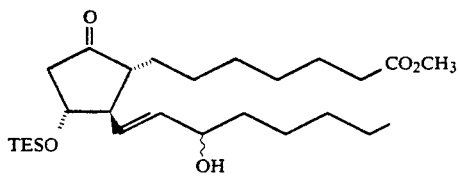

What is claimed is:

1. A process for preparing prostaglandin derivatives comprising reacting in a single reaction vessel a bis tin ethylene of the formula

wherein R is independently lower alkyl, alkenyl, phenyl, naphthyl, phenanthryl or thienyl; with an organo metal compound of the formula $R^1M_n$ wherein n is either 1 or 2, M is selected from lithium, copper and magnesium, and $R^1$ is selected from lower alkyl or a group having the formula

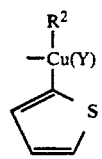

wherein
Y is —CN, —SCN, —OSO$_2$CF$_3$ or —S-phenyl, and $R^2$ is lower alkyl;

adding a compound selected from an epoxide, aldehyde and a ketone;
adding an organo lithium compound and a cuprate complex and reacting with a cyclopentenone compound of the formula

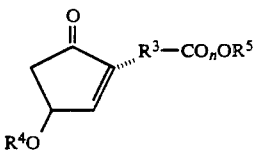

wherein
n is 0 or 1; $R^3$ is an alkyl, alkenyl, alkynyl group of 1 to 6 carbon atoms
$R^4$ is an oxygen protector group; and
$R^5$ is hydrogen or a lower alkyl group to produce a prostaglandin intermediate.

2. A process as recited in claim 1 wherein the organo metal compound has the formula

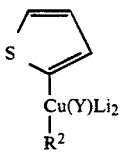

3. A process as recited in claim 2 wherein Y is —CN.
4. A process as recited in claim 3 wherein $R^2$ is methyl.
5. A process as recited in claim 1 wherein the organo lithium compound has the formula

and $R^1$ is a lower alkyl group.
6. A process as recited in claim 1 wherein R is a lower alkyl group.
7. A process as recited in claim 6 wherein R is a butyl group.
8. A process as recited in claim 1 wherein an epoxide is added.
9. A process as recited in claim 1 wherein an aldehyde is added.
10. A process as recited in claim 1 wherein a ketone is added.
11. A process as recited in claim 1 wherein M is lithium.
12. A process as recited in claim 1 wherein the organo lithium compound is n-butyl lithium.
13. A process as recited in claim 1 wherein the cuprate complex has the formula

wherein n is 1 or 2 and $R^8$ is a lower alkyl.
14. A process as recited in claim 1 further comprising the step of acidifyinq the prostaglandin intermediate to deprotect the hydroxyl group on the cyclopentane ring.

* * * * *

UNITED STATES PATENT AND TRADEMARK OFFICE
CERTIFICATE OF CORRECTION

PATENT NO. : 5,075,478

DATED : December 24, 1991

INVENTOR(S) : James R. Behling, et al

It is certified that error appears in the above-identified patent and that said Letters Patent is hereby corrected as shown below:

Column 2, line 58, reading "3,3 dimethyl 3 methoxy" should read -- 3,3-dimethyl-3-methoxy --

Column 3, line 31, reading "derivatives" should read -- derivatives. --

Column 6, line 56, reading "bis-rin" should read -- bis-tin --

Column 7, structure (7), reading

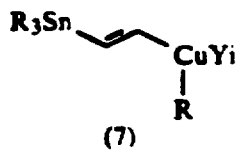  should read  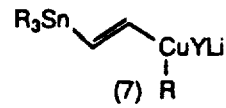

Column 7, line 40, reading "(E)-bis (tributylstannyl)" should read -- (E)-bis-(tributylstannyl) --

Column 8, line 68 reading "(5.59 q," should read -- (5.59 g --

UNITED STATES PATENT AND TRADEMARK OFFICE
CERTIFICATE OF CORRECTION

PATENT NO. : 5,075,478

DATED : December 24, 1991

INVENTOR(S) : James R. Behling, et al

It is certified that error appears in the above-identified patent and that said Letters Patent is hereby corrected as shown below:

Column 9, line 17, reading "2 thienylcyanocuprate" should read -- 2-thienylcyanocuprate --

Column 9, line 57, which is blank should have a heading inserted reading -- EXAMPLE 3 --

Column 10, line 1, reading "H2O" should read -- $H_2O$ --

Column 10, line 18, reading "structure" should read -- structure, --

Column 13, line 49, reading "2 thienylcyanocuprate," should read -- 2-thienylcyanocuprate, --

Column 13, line 64, reading "2 lithiothiophene" should read -- 2-lithiothiophene --

Column 13, line 65, reading "at 78°" should read -- at -78° --

Column 14, line 7, reading "termperature" should read -- temperature --

Column 14, line 8, reading "at 78°" should read -- at -78° --

Column 14, line 21, reading "quenced" should read -- quenched --

UNITED STATES PATENT AND TRADEMARK OFFICE
CERTIFICATE OF CORRECTION

PATENT NO. : 5,075,478

DATED : December 24, 1991

INVENTOR(S) : James R. Behling, et al

It is certified that error appears in the above-identified patent and that said Letters Patent is hereby corrected as shown below:

Column 14, line 31, reading "chromotography" should read
-- chromatography --

Column 16, line 60, reading "acidifyinq" should read
-- acidifying --

Signed and Sealed this

Twenty-third Day of November, 1993

Attest:

BRUCE LEHMAN

Attesting Officer

Commissioner of Patents and Trademarks